United States Patent [19]

Scherr

[11] Patent Number: 5,674,524
[45] Date of Patent: Oct. 7, 1997

[54] ALGINATE FIBROUS DRESSING AND METHOD OF MAKING THE SAME

[75] Inventor: George H. Scherr, Park Forest, Ill.

[73] Assignee: DeRoyal Industries Inc., Powell, Tenn.

[21] Appl. No.: 548,750

[22] Filed: Oct. 26, 1995

Related U.S. Application Data

[63] Continuation of Ser. No. 263,971, Jun. 15, 1994, abandoned.

[51] Int. Cl.$^6$ .................................................. A61K 9/70
[52] U.S. Cl. ........................ 424/445; 424/443; 602/41; 604/304
[58] Field of Search ............................. 424/443, 431, 424/445; 602/41–46, 58; 604/304

[56] References Cited

U.S. PATENT DOCUMENTS

| | | | |
|---|---|---|---|
| 4,685,914 | 8/1987 | Holtman | 604/368 |
| 5,197,945 | 3/1993 | Cole et al. | 602/49 |
| 5,238,685 | 8/1993 | Wren | 424/445 |
| 5,256,477 | 10/1993 | Mahoney | 428/283 |

FOREIGN PATENT DOCUMENTS

| | | |
|---|---|---|
| 3218076 | 1/1983 | Germany. |
| WO92/22285 | 12/1992 | WIPO ................ A61K 9/70 |

OTHER PUBLICATIONS

"Alginates and Alginate Fibers in Clinical Practice," by George H. Scherr, *Wounds: A Compendium of Clinical Research and Practice*, Health Management Publications, Inc. 1992, pp. 74–80.

*Primary Examiner*—Gollamudi S. Kishore
*Attorney, Agent, or Firm*—Luedeka, Neely & Graham

[57] ABSTRACT

The specification discloses an alginate dressing comprising a fibrous alginate layer needle punched to a non-alginate backing web such that fibers from the alginate layer penetrate into and are interlocked with the backing web thereby affixing the alginate layer to the backing web. The dressing exhibits improved absorbency and long-term stability when used in the treatment of wounds. The dressing also eliminates the need for adhesives and secondary dressings for retaining an alginate fibrous dressing on a wound site.

10 Claims, No Drawings

ALGINATE FIBROUS DRESSING AND METHOD OF MAKING THE SAME

This is a continuation of application Ser. No. 08/260,971, filed Jun. 15, 1994 now abandoned.

FIELD OF THE INVENTION

The present invention relates to novel alginate compositions useful in the medical and veterinary fields and to methods of making same. More specically, the invention relates to novel compositions of alginate which can be prepsred in fibrous form and which may be utilized in the preparation of dressings where the dressing contains a non-alginate backing.

DESCRIPTION OF THE PRIOR ART

Alginates are polysaccharide-like compounds extracted from certain seaweeds and have been described in great detail in numerous reports, literature, and patents (Kelco Algin, 2nd Ed., pgs. 1–50, Kelco Co., Chicago, Ill. 60606; Alginates in Pharmaceuticals and Cosmetics, Alginate Industries, Ltd., London W.O.2, Great Britain; Properties of Alginates, R. H. McDowell, Alginate Industries, Ltd., London, England, 1955; Alginate Adjuvant and Alginate Fibers, a literature Survey, George H. Scherr, Governors State University, Park Forest South, Ill.; U.S. Pat. Nos. 1,778 688; 1,814,986; 2,477,861; and others)

One of the salient attributes of alginates is their ability to form gels when they react with certain polyvalant cations. Thus, solutions of sodium alginate which are soluble in water and other aqueous media will form gels when reacted with certain polyvalant ions which include calcium, zinc, aluminum, copper, and silver. The formation of alginate gels has been described in the literature and in patents (Kelco, ibid; U.S. Pat. Nos. 2,420,308; 3,349,079 and 3,386,921). The polyvalant ion-alginate gels so formed, such as calcium alginate, are insoluble in water but will dissolve in solutions of sodium salts of organic acids such as sodium hexametaphosphate, sodium glycerophosphate and sodium citrate.

Alginate solutions when injected into an appropriate solution containing calcium chloride, as an example, will result in the precipitation of an alginate thread. Such alginate threads when dried can be cut into alginate staple and prepared as woven or nonwoven dressings which have application in the medical and veterinary fields.

A study describing the use of absorbable alginate fibers in the surgical applications was made by Blaine (George Blaine, Experimental Observations on Absorbable Alginate Products in Surgery, Annals of Surgery, January, 1949, pp. 102–114). Alginate fibers and films were shown to enhance the rate of healing in experimental animals as contrasted with controls. Fairbairn and whittet (J. W. Fairbairn and T. D. Whittet, Absorbable Haemostatics: Their Uses and Identification. The Pharmaceutical Journal, Feb. 28, 1948, pp. 149–150), and Oliver & Blaine (British J. of Surgery, 37:1–4, 1950), reported that alginate fibers when used as absorbable hemostatic agents had significant advantages over oxidized cellulose in that oxidized cellulose inactivated penicillin whereas alginate did not and also that oxidized cellulose could not be sterilized by heat whereas alginate fibers could readily be sterilized by heat without being significantly altered in physical and chemical characteristics.

Additional reports of the hemostatic properties of alginates have been made by Gosset (texte de la communication faite le 16 mars 1949, a l'Academie de Chirurgie de Paris Hopitaux de Paris); Rumble (Twenty-Five Dental Cases Treated With Absorbable Alginate Wool, British Dental Journal, Vol. LXXXVI, No. 8, 1949); Clifton (A New and Effective Haemostatic Agent, Science, Vol. 103, No. 2681, Pg. 634, 1946); Clarice Bray (Results With Alginate Materials in the Casualty Department of Croydon General Hospital, Croydon General Hospital, Croydon, U.K.); L. J. Allen (Oral Use of Absorbable Alginate Derivatives to Arrest and Prevent Postextraction Hemorrhage, Oral Surgery, Oral Medicine, and Oral Pathology, Vol. 6, No. 2, pp. 336–338, 1953); E. S. Hurwitt, et al. (New Surgical Absorbable Hemostatic Agent, American Journal of Surgery, Vol. 100, 1960).

The obvious utility of an alginate dressing has resulted in a number of alginate dressings, woven or unwoven, being introduced in the marketplace, and these have been described in the literature of the various manufacturers such as:

Kaltostat Wound Dressing and Packing,
Calgon Vestal Laboratories,
a division of Calgon Corporation,
a subsidiary of Merck & Co, Inc.
St. Louis, Missouri 1682-306-192, rev. 1/92:
Algiderm, Alginate Wound Dressing,
Viaderm Pharmaceuticals, Inc.,
Carlsbad, California, 92008
Algosteril
Johnson & Johnson Medical, Inc.
Arlington, Texas 76004-0130
June, 1991, 2490 11-0
Sorbsan Topical Wound Dressing
Dow B. Hickam, Inc.
Sugar Land, Texas 77478
rev. 2/90
Kaltostat Wound Dressing,
Calgon Vestal Laboratories,
a division of Calgon Corporation
a subsidiary of Merck & Co., Inc.
St. Louis, Missouri 63133 - 1682-101-010

Since alginate fibers are much weaker fibers than most other synthetic fibers in use in the textile industry, and also because alginate fibers in the form of a dressing, when exposed to an exudating wound, become very soft and hydrocolloidal in nature, it has been almost uniformly recommended by all manufacturers of alginate dressings that a secondary dressing is necessary and should be applied over the alginate dressing after the latter has been utilized to cover a wound.

The application of an alginate dressing which requires the recommendation by the manufactuers that a secondary dressing has to be applied over the alginate dressing, is a laborious and duplicative procedure that is time consuming and adds extra work and cost to the application of dressings where required. A number of alternative means have been proposed in order to obviate the need of applying two separate dressings, one of which is alginate, to the wound. Thus, U.S. Pat. No. 5,238,685 teaches construction of an alginate dressing which has a backing layer affixed to it with an adhesive and in which such adhesive extends beyond the dressing so that it may adhere to the non-wounded part of the body. This invention necessarily places certain restrictions on the construction of such a dressing in that the adhesive used must be moisture vapor permiable, and must be unaffected by water. In addition, the alginate fibers utilized to prepare the alginate dressing must have a calcium alginate to sodium alginate ratio of 80:20. Further, a silicone release paper must be applied to the adhesive's surface to protect it prior to it being placed into use and therefore, may not be non-toxic to tissues and that the dressing itself can not be trimmed without destroying the adhesive section that is designed to affix to the skin, results in a dressing which is complex to construct, composed of a multiplicity of parts which would add to the cost of manufacture and is highly restrictive in that the alginate fibers must be of a certain composition.

In order to strenghen a non-woven alginate dressing, it has become well accepted in the field to needle-punch the web of alginate fibers using conventional needle-punching procedures. The needles thus employed contains a number of barbs and when the needles enter a web of alginate or other fibers, the fibers become entangled due to the barbs penetrating through layers of the fibrous matt and catching a number of fibers on the barbs and thus entangling them. Despite the fact that needle-punching a web of alginate fibers in non-woven form substantially strengthens a dressing thus prepared from alginate fibers, it is still recommended by the manufacturers of alginate dressings that a secodary dressing be applied over the alginate dressing because the alginate fibers become very weak and hydrocolloidal in nature when the alginate dressing is applied to an exudating wound.

SUMMARY OF THE INVENTION

It is, therefore, an object of the present invention to provide a fibrous backing to an alginate dressing in a manner so that the fibrous backing becomes an integral part of the dressing and so obviates the necessity of applying a secondary dressing when an alginate dressing is utilized in an open or exudating wound.

It is also an object of the invention to provide a fibrous alginate dressing which can be needle-punched to a non-alginate backing simultaneously as the alginate dressing is being needle-punched thus being conserving in time, labor, and money in fabricating an alginate dressing with a non-alginate backing.

Other objects and advantages will become apparent from the following description and appended claims:

DESCRIPTION OF THE PREFRRED EMBODIMENTS

In the practice as currently followed, calcium alginate fibers are prepared and cut into staple of desired length and such alginate staple can be prepared in a non-woven web utilizing various carding machines which will prepare the web by an airblown process or for example by a cross-lap process. The alginate web thus coming out of the machine can be fed directly into a conventional needle-punching machine to interlock the fibers in order to enhance the overall strength of the alginate web. The following examples indicate the applications of our invention in affixing a non-alginate backing to the non-woven alginate web.

EXAMPLE 1

Alginate fibers are prepared, dried, and cut into two-inch staple widths. The calcium alginate staple fiber is fed into a hopper of a cross-lap machine as is well known in the textile industry and a 15-inch width of non-woven alginate web is deposited onto a moving belt. The web is picked up by two belts driven by rollers and cross-lapped across a belt moving perpendicular to the first belt. The lapping operation deposits the alginate web onto a moving belt which has been fed a 15-inch width of an acrylic-cotton continuous backing. The backing now contains on its surface a cross-lapped alginate web, and the two components continue to be moved into the needle-punching machine.

The needle-punching machine can be adjusted so that the barb needles penetrate the alginate web and penetrate a depth into the non-alginate backing underneath in order to so entangle the fibers of the alginate and the non-alginate backing where the two layers meet.

This is readily achieved by needle-punching through the thickness of the alginate web and enter the barbed needles approximately 1–2 mm into the acrylic-cotton backing to be affixed to the alginate web; in order to ensure that the fibers are thus interlocked.

By such needle-punching procedure, a single strenghened web is produced which on one side contains the alginate fibers and on the back side contains a non-alginate backing of arcrylic cotton.

Since time cross-lapping of alginate fibers results in the same width as the backing onto which the alginate is laid, the two layers are locked together as they come out of the needle-punching machine after which they may be wound on a continous roll.

EXAMPLE 2

The calcium alginate fibers are prepared as described in Example 1 and result in a non-woven web which is then deposited by the cross-lapping operation onto a backing composed of an elastic polyurethane foam.

The rest of the procedure including needle-punching is as described in Example 1 above.

EXAMPLE 3

Alginate fibers are prepared and cut into staple as described in Example 1 above and the alginate fibers are airblown in a Rando machine onto a moving belt where they form a web having a diameter of 48 inches. The alginate fiber web is thus deposited onto a sheet of an acrylic-cotton backing having a width of 48 inches and which is fed at exactly the same rate on the moving belt as the non-woven alginate web coming off the Rando machine. The two layers are then fed into a needle-punching operation as described in Example 1 and the two webs become affixed to each other by interlocking of their fibers.

EXAMPLE 4

The calcium alginate fibers are prepared as described in Example 1 above and fed into a Rando machine exactly as in Example 3, except that an elastic polyurethane backing is utilized having the same diameter as the width of the non-woven alginate web.

The two layers are then fed into a needle-punching operation as described in Example 1 and the alginate web becomes affixed to the elastic polyurethane backing by the interlocking of the alginate fibers into the polyurethane sheet.

The novelty of the invention we described herein provides a number of significant advantages in the use of an alginate dressing:

1. The overall strength of the alginate dressing is substantially enhanced by it being affixed to a backing. Thus, an alginate non-woven dressing which has been needle-punched and tested in an SHMPO tensiometer in which is affixed ½ inch width by 1½ inch length strip of the needle-punched non-woven alginate dressing will break at 2.8 lbs.

of tension. The same dressing needle-punched to the acrylic-cotton backing as described in Example 1 will break at 4.3 lbs. of tension. The identical dressing affixed to the polyurethane foam backing as described in Example 4 will break at 8.4 lbs. of. tension.

2. Alginate dressings already affixed to a backing when thus supplied as one unit to the medical or veterinary users requiring such dressings for man or animals obviates the need of procuring a secondary dressing in order to cover the alginate as is currently mandated in the profession for those alginate dressings in the market.

3. Alginate dressings with a backing will require less frequent changing especially if placed on an exudating wound because the backing will permit a greater amount of fluid to be absorbed by the alginate then when the alginate is used without such backing.

4. Where a dressing is required to be placed on a part of the body that may be frequently in motion or bent, such as the back of a patient or an elbow joint, the alginate dressings without an extra covering will easily break because of their fragility and affixing a backing, especially one such as a flexible polyurethane foam backing, directly to the alginate will avoid such distortion and/or breaking.

5. An additional advantage of an alginate dressing containing a backing as described herein ensues from the ease with which an adhesive strip can be placed on the backing and hold the alginate dressing in place. Because alginate becomes hydrocolloidal in an exudating wound, the adhesive strip would become moist and would easily dissasociate from the alginate dressing, a result that is obviated by the use of a backing as we describe herein.

6. The needle-punching that has been utilized in the invention described herein by affixing the alginate fiber web to a backing requires no chemicals, adhesives, or heat treatment in order to bond the alginate fibers to the non-alginate backing. This is a particular advantage in that no chemicals are added which might in some way be deleterious to a healing wound, or could even be absorbed into the tissues of a wound which could interfer with the healing process.

It will be appreciated that the foregoing description and illustrative examples relating to the particular constructions of a non-woven alginate dressing with a non-alginate backing affixed to it are really exemplary of illustrative and preferred forms of the invention. However, the invention is not limited to the precise constructions described herein.

For example, in the examples cited herein the alginate staple fibers are described as being of a two-inch length. It is clear that the staple fibers can be shorter of greater than two-inch length depending upon the particular carding machine utilized in preparing the non-woven alginate web without deviating in any way from the scope and the novelty of the invention described herein.

The examples cited herein describe the utilization of an acrylic-cotton backing an a polyurethane foam flexible backing as being affixed by needle-punching to the alginate web. However, backings having other properties and of varying other compositions may be utilized without departing from the present invention as long as the alginate is of a fibrous nature that can be needle-punched to the backing to be affixed to it.

In the examples cited herein, two carding machines are described in which one provides an airblown non-woven web and the other provides a web by cross-lapping. It is clear that many other carding machines are available which can provide a non-woven web from alginate staple without in any way deviating from the scope or the novelty of the invention herein described.

In the examples given we describe the fibers as being of calcium alginate but alginate fibers can be prepared as sodium-calcium fibers wherein the proportions of sodium alginate and calcium alginate can vary over a very broad range and can be utilized to prepare woven or non-woven alginate dressings which would lend themselves to the needle-punching operation to a non-alginate backing as we describe herein.

In the examples given we describe the needle-punching to penetrate the alginate web and penetrate into the non-woven backing approximately 1–2 mm. It is clear that depending upon the thickness of the alginate web and the thickness of the backing that is desired, the penetration of the barb needles utilized in needle-punching may be required to penetrate more or less but should carry the alginate fibers on the penetration into the backing in order that the fibers of the alginate and the fibers of the backing conttnous to the alginate are angled so that the alginate web and the non-alginate backing thus affixed to each other.

It is also clear that fibers can be prepared as a woven cloth as well as a non-woven cloth or in a knitted form, and such algtnate cloths may be utilized in being affixed by needle-punching to a backing without in any way deviating from the scope or novelty of the invention described herein.

I claim:

1. An alginate dressing comprising a fibrous alginate layer juxtaposed with a non-alginate backing web, wherein the alginate layer is strengthened by needle punching and wherein the alginate layer is needle punched completely through the alginate layer to the backing web such that fibers from the alginate layer penetrate into and are interlocked with the backing web thereby affixing the alginate layer to the backing web.

2. A fibrous alginate dressing as claimed in claim 1, wherein the alginate in the alginate layer is selected from the group consisting of sodium alginate, calcium alginate and mixtures thereof.

3. A fibrous alginate dressing as claimed in claim 2, wherein the backing web comprises a fabric composed of acrylic and cotton fibers.

4. A fibrous alginate dressing as claimed in claim 1, wherein the backing web comprises a fabric composed of acrylic and cotton fibers.

5. A fibrous alginate dressing as claimed in claim 2, wherein the backing web comprises a polyurethane foam sheet.

6. A fibrous alginate dressing as claimed in claim 1, wherein the backing web comprises a polyurethane foam sheet.

7. A fibrous alginate dressing as claimed in claim 1, wherein the alginate layer is woven.

8. A fibrous alginate dressing as claimed in claim 1, wherein the alginate layer is knitted.

9. A fibrous alginate dressing as claimed in claim 1, wherein the alginate layer is non-woven.

10. A fibrous alginate dressing as claimed in claim 1, wherein the alginate layer is crosslapped on the backing web.

* * * * *

UNITED STATES PATENT AND TRADEMARK OFFICE
CERTIFICATE OF CORRECTION

PATENT NO. : 5,674,524
DATED : October 7, 1997
INVENTOR(S) : George H. Scherr

It is certified that error appears in the above-identified patent and that said Letters Patent is hereby corrected as shown below:

Column 1, line 12, delete "prepsred" and insert --prepared--.

Column 1, line 51, delete "1949" and insert --1947--.

Column 1, line 54, delete "whittet" and insert --Whittet--.

Column 5, line 5, change "of." to --of--.

Column 6, line 22, delete "continous" and insert --continuous--.

Signed and Sealed this

Seventeenth Day of February, 1998

Attest:

BRUCE LEHMAN

*Attesting Officer*     *Commissioner of Patents and Trademarks*